US011684753B2

United States Patent
Hakkens et al.

(10) Patent No.: US 11,684,753 B2
(45) Date of Patent: Jun. 27, 2023

(54) INVASIVE MEDICAL DEVICE AND MANUFACTURING METHODS

(71) Applicant: KONINKLIJKE PHILIPS N.V., Eindhoven (NL)

(72) Inventors: Franciscus Johannes Gerardus Hakkens, Eersel (NL); Cornelis Gerardus Maria De Haas, Nuenen (NL); Johannus Gerardus Van Beek, Budel (NL); Franciscus Reinier Antonius Van Der Linde, Schijndel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 409 days.

(21) Appl. No.: 16/649,029

(22) PCT Filed: Sep. 26, 2018

(86) PCT No.: PCT/EP2018/076069
§ 371 (c)(1),
(2) Date: Mar. 19, 2020

(87) PCT Pub. No.: WO2019/063592
PCT Pub. Date: Apr. 4, 2019

(65) Prior Publication Data
US 2020/0289790 A1 Sep. 17, 2020

(30) Foreign Application Priority Data

Sep. 28, 2017 (EP) .................................... 17193686

(51) Int. Cl.
*A61M 25/01* (2006.01)
*A61M 25/00* (2006.01)
*A61M 25/09* (2006.01)

(52) U.S. Cl.
CPC .... *A61M 25/0158* (2013.01); *A61M 25/0015* (2013.01); *A61M 25/0026* (2013.01);
(Continued)

(58) Field of Classification Search
CPC .......... A61M 25/0158; A61M 25/0026; A61M 25/09; A61M 2025/09141;
(Continued)

(56) References Cited

U.S. PATENT DOCUMENTS

| 4,799,474 A * | 1/1989 | Ueda ............... A61M 25/09033 |
| | | 604/291 |
| 4,930,494 A | 6/1990 | Takehana |

(Continued)

FOREIGN PATENT DOCUMENTS

| EP | 1010440 A2 | 6/2000 |
| WO | 199744089 A1 | 11/1997 |

(Continued)

OTHER PUBLICATIONS

International Search Report & Written Opinion of PCT/EP2018/076069, dated Feb. 12, 2019.

*Primary Examiner* — James D Ponton
*Assistant Examiner* — Neeraja Gollamudi (57) ABSTRACT

An invasive medical device (10) is disclosed comprising a flexible sheath (11) enveloping at least one lumen (17, 17') comprising an electrically conductive wire (20) including a deformable actuator (21) for deforming a section of the invasive medical device in response to an electric current provided through the electrically conductive wire, wherein the flexible sheath comprises a set of apertures (31) extending through the flexible sheath to the at least one lumen, said apertures being filled with an adhesive (33) anchoring the deformable actuator to the flexible sheath. A manufacturing method for such an invasive medical device (10) is also disclosed.

9 Claims, 4 Drawing Sheets

(52) U.S. Cl.
CPC ... *A61M 25/09* (2013.01); *A61M 2025/09108* (2013.01); *A61M 2025/09141* (2013.01)

(58) Field of Classification Search
CPC .. A61M 2025/0058; A61M 2205/0272; A61M 2205/0888; A61M 2205/0283; A61M 2205/0294; A61M 25/003; A61M 25/0067
See application file for complete search history.

(56) References Cited

U.S. PATENT DOCUMENTS

| | | | |
|---|---|---|---|
| 5,349,964 | A | 9/1994 | Imran |
| 5,357,979 | A | 10/1994 | Imran |
| 5,409,453 | A * | 4/1995 | Lundquist .......... A61B 17/3403 607/99 |
| 5,419,767 | A | 5/1995 | Eggers |
| 5,531,685 | A | 7/1996 | Hemmer |
| 2005/0245862 | A1 | 11/2005 | Seward |
| 2006/0079787 | A1* | 4/2006 | Whiting ............ A61M 25/0041 600/466 |
| 2007/0244550 | A1 | 10/2007 | Eidenschink |
| 2008/0147000 | A1* | 6/2008 | Seibel ............... A61M 25/0155 604/528 |
| 2010/0249568 | A1 | 9/2010 | Stehr |
| 2014/0135686 | A1 | 5/2014 | Jimenez |

FOREIGN PATENT DOCUMENTS

| | | | |
|---|---|---|---|
| WO | 199839048 A2 | 9/1998 | |
| WO | 2017136729 A1 | 8/2017 | |
| WO | WO-2018170537 A1 * | 9/2018 | ......... A61B 18/1492 |

\* cited by examiner

INVASIVE MEDICAL DEVICE AND MANUFACTURING METHODS

CROSS-REFERENCE TO PRIOR APPLICATIONS

This application is the U.S. National Phase application under 35 U.S.C. § 371 of International Application No. PCT/EP2018/076069, filed on Sep. 26, 2018, which claims the benefit of European Patent Application No. 17193686.7, filed on Sep. 28, 2017. These applications are hereby incorporated by reference herein.

FIELD OF THE INVENTION

The present invention relates to an invasive medical device comprising a flexible sheath enveloping at least one lumen comprising an electrically conductive wire including a deformable actuator for deforming a section of the invasive medical device in response to an electric current provided through the electrically conductive wire.

The present invention further relates to a method of manufacturing such an invasive medical device.

BACKGROUND OF THE INVENTION

Steerable invasive medical devices, e.g. steerable catheters or guidewires, are commonly used in medical procedures in order to steer the flexible tip of the invasive medical device towards a target area within a patient's body, or to steer the flexible tip around an obstacle within the patient's body, such as a stenosis for example.

An example of such a steerable invasive medical device is disclosed in US 2010/0249568 A1 in which a catheter is disclosed comprising a shape memory wire terminating at a distal end of the catheter. The distal end of the shape memory wire may be embedded in an adhesive, such as a UV-cured adhesive or alternatively the distal end of the flexible distal tip segment includes one of a plug or a seal, and the plug or the seal comprises an adhesive, such as a UV-cured adhesive.

Such gluing of the shape-memory wire is however less straightforward if the section of the shape-memory wire to be secured is an intermediate section of the shape-memory wire, e.g. to introduce a steerable portion into the invasive medical device in between the distal tip and the proximal end, e.g. the handle end, of the invasive medical device.

This is typically overcome by securing the shape-memory wire in the lumen of the invasive medical device during its assembly. However, this is not without problems either. Such an assembly method for example may include integrating an actuator such as a shape memory alloy actuator or an electroactive polymer (EAP) actuator during invasive medical device assembly, e.g. by assembling several polymer extrusions on mandrels, after which the extrusions are braided and laminated at elevated temperatures, e.g. temperatures in a range of 160–220° C. in case the polymer used is a thermoplastic elastomer such as Pebax as marketed by the Arkema Corporation by way of non-limiting example. However, this elevated temperature step required during the lamination process typically affects the deformable actuator within the invasive medical device.

For example, where the deformable actuator is based on a shape memory material such as a shape memory alloy, the elevated temperature typically causes the shape memory material to transition from a deformed martensite phase to an austenite phase, which typically causes the material to shrink and deforms the invasive medical device, after which the material cools to a twinned martensite phase. In order to rectify this shrinkage, a considerable stretching force must be applied to the elongation direction of the invasive medical device in order to return the shape memory material to the deformed martensite phase. This typically requires the integration of an antagonist such as a spring in the invasive medical device, which increases the thickness (diameter) and stiffness of the invasive medical device, which is unwanted.

Similarly, where the deformable actuator is based on an EAP, the elevated temperatures can degrade the EAP, thereby comprising the performance of the deformable actuator. What is more, in such assembly methods a large number of parts, e.g. actuators, mandrels, antagonists such as springs, liners and so on have to be kept aligned during assembly by thermal reflowing, which is labour-intensive and often leads to imprecise results.

SUMMARY OF THE INVENTION

The present invention seeks to provide an invasive medical device in which the actuator can be more precisely aligned within the invasive medical device.

The present invention further seeks to provide a method of manufacturing such an invasive medical device.

According to an aspect, there is provided an invasive medical device comprising a flexible sheath enveloping at least one lumen, said at least one lumen comprising an electrically conductive wire including a deformable actuator for deforming a section of the invasive medical device in response to an electric current provided through the electrically conductive wire, wherein the flexible sheath comprises a set of apertures extending through the flexible sheath to the at least one lumen, said apertures being filled with an adhesive anchoring the deformable actuator to the flexible sheath.

Such an invasive medical device has a precisely aligned deformable actuator, owing to the fact that the deformable actuator is secured in the invasive medical device post-manufacture of the flexible sheath of the invasive medical device, thereby avoiding the exposure of the deformable actuators to the aforementioned elevated processing temperatures, thus avoiding deformation and/or degradation of the deformable actuator, for example in the case where the deformable actuator comprises a shape memory material or an electro-actuated polymer.

In an embodiment, the invasive medical device further comprises a biocompatible sleeve around a section of the flexible sheath comprising the set of apertures. This for example may be useful to protect a patient from exposure to the adhesive used to anchor the deformable actuator to the flexible sheath, which may be required in case of the adhesive itself not being biocompatible.

The biocompatible sleeve for example may comprise a shrink wrap polymer, which has the advantage that the biocompatible sleeve may be formed in a simple and straightforward manner by shrinking the shrink wrap polymer sleeve into place over the section of the flexible sheath comprising the set of adhesive-filled apertures. Furthermore, many shrink wrap polymers are inexpensive and biocompatible, e.g. polyethylene terephthalate (PET) polymers, (polytetrafluoroethylene) PTFE polymers, polymer blends such as polyethylene/polypropylene blends and so on, making them particularly suitable for forming the biocompatible sleeve.

In an embodiment, the at least one lumen comprises a first lumen comprising a first electrically conductive wire including a first deformable actuator; and a further lumen comprising a further electrically conductive wire including a further deformable actuator. This for example is advantageous as the first deformable actuator may act as antagonist of the further deformable actuator and vice versa, such that the need for a separate antagonist, e.g. spring, may be avoided. More generally speaking, the inclusion of multiple deformable actuators within the invasive medical device may increase the ability to steer the invasive medical device in desired directions during invasive medical procedures in which the invasive medical device is being used.

In another embodiment, the at least one lumen comprises a first lumen comprising a portion of the first electrically conductive wire including a portion of the deformable actuator; and a further lumen comprising a further portion of the first electrically conductive wire including a further portion of the deformable actuator. In this embodiment, a larger deformation force can be applied to the deformable region of the flexible sheath due to the presence of the deformable actuator portions in adjacent lumens.

Where the flexible sheath comprises a polymer reinforced by a metal braiding, the adhesive preferably extends through the metal braiding such that the structural integrity of the flexible sheath is not compromised by the presence of the set of apertures, whilst allowing the deformable actuator to be anchored against the flexible sheath.

In example embodiments, the invasive medical device is a multi-lumen catheter or guide wire.

According to another aspect, there is provided a method of manufacturing an invasive medical device, the method comprising producing a flexible sheath enveloping at least one lumen; cutting a set of apertures through the flexible sheath, said apertures exposing one of the at least one lumen; inserting an electrically conductive wire including a deformable actuator for deforming a section of the invasive medical device in response to an electric current provided through the electrically conductive wire into the one lumen, thereby aligning the deformable actuator with the set of apertures; and anchoring the deformable actuator to the flexible sheath by filling the apertures of said set with an adhesive contacting the deformable material portion.

In accordance with embodiments of the method of the present invention, an invasive medical device may be manufactured in any suitable manner such as in the manner described above in the background section of this application, after which a set of apertures, i.e. through holes, are cut through the flexible sheath exposing designated areas of one or more lumens within the invasive medical device in which the deformable actuator is to be anchored to the flexible sheath. Subsequently, the insertion of the electrically conductive wire including the deformable actuator into this one or more lumen ensures that the actuator can be anchored within the invasive medical device in precise alignment with the flexible sheath using an adhesive, in particular an adhesive that can be cured at a temperature below a critical temperature at which the deformable actuator is physically altered, e.g. through a shape change or an irreversible degradation of the actuator material, such as an adhesive that can be cured at room temperature (about 25° C.). As will be understood, in embodiments of the method of the present invention the set of apertures may provide access to multiple lumens such that multiple deformable actuators in different lumens may be anchored to the flexible sheath in accordance with the method, thereby providing an invasive medical device comprising a plurality of such deformable actuators. This may be used to make the invasive medical device more steerable and/or to alternate actuation of such deformable actuators such that a first deformable actuator may act as an antagonist of a further deformable actuator and vice versa as previously explained.

In an embodiment, cutting the set of apertures through the flexible sheath comprises laser-cutting said set of apertures. This has the advantage that the amount of energy directed at the regions of the flexible sheath in which the apertures are formed can be precisely controlled, which for example is advantageous in embodiments in which the flexible sheath comprises a polymer reinforced with a metal braiding, as the precisely controlled amount of energy ensures that the polymer is selectively removed whilst leaving the metal braiding intact, thereby providing access to the lumen(s) of interest without significantly compromising the structural integrity of the flexible sheath.

The method may further comprise applying a biocompatible coating around a section of the flexible sheath comprising the plurality of apertures. This ensures that the entire surface of the flexible sheath exposed to the patient remains biocompatible in case of the use of adhesives in the set of apertures that are themselves not biocompatible. In a particular example, applying the biocompatible coating comprises applying a shrink-wrap polymer around said section and shrinking the shrink-wrap polymer to form the biocompatible coating, as this is a particularly straightforward and cost-effective manner of forming such a biocompatible coating, although it should be understood that the biocompatible coating may be formed in any suitable manner.

In an embodiment, inserting the electrically conductive wire including the deformable actuator into one of the at least one lumen comprises inserting a first portion of the deformable actuator into a first lumen; and looping a second portion of the deformable material into a second lumen at a distal end of the flexible sheath, the method further comprising affixing a device tip to said distal end after said inserting. This has the advantage that the deformable actuator may be spread across multiple lumens, which may increase the degree of deformation of the invasive medical device over a smaller area of the flexible sheath, thereby yielding a particularly bendable invasive medical device.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
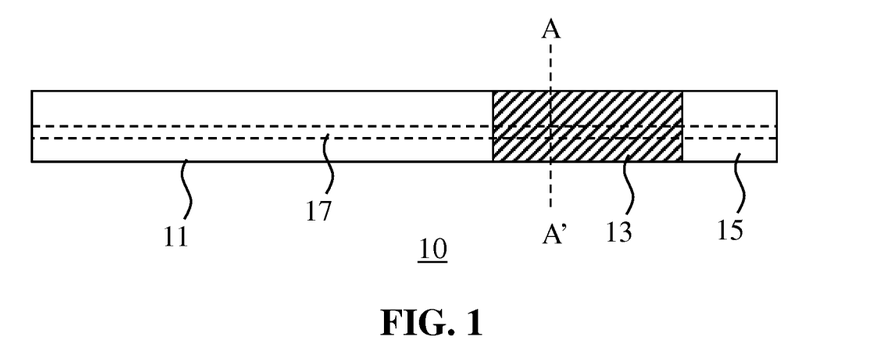
FIG. 1 schematically depicts an elongate flexible invasive medical device.
Figure 2:
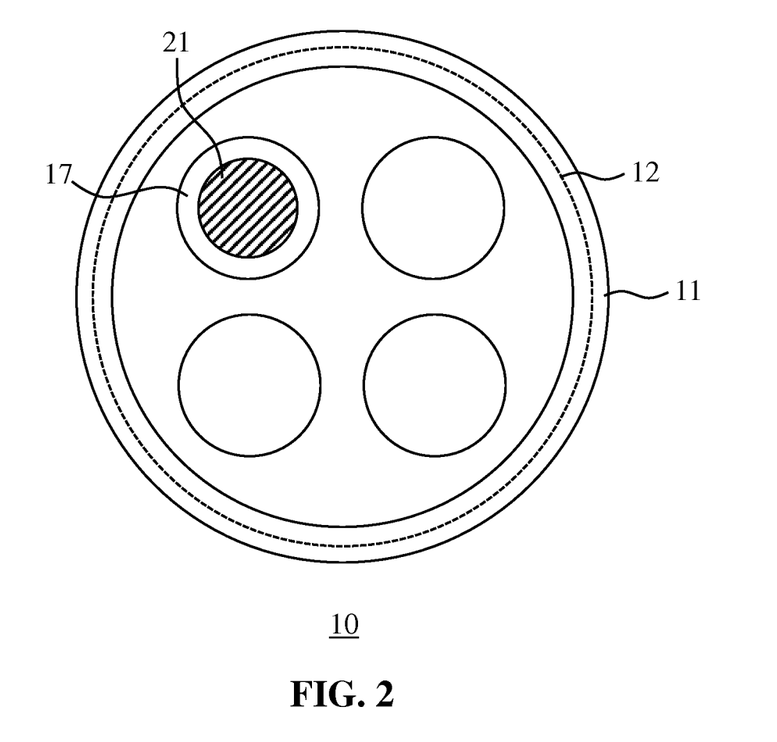
FIG. 2 schematically depicts a cross-sectional view of the elongate flexible invasive medical device of FIG. 1 along the line A-A'.

FIG. 1 schematically depicts an example embodiment of an invasive medical device 10, such as a catheter or a guide wire, with FIG. 2 schematically depicting a cross-section of this invasive medical device 10 along the line A-A'. The invasive medical device 10 typically is an elongated invasive medical device having a flexible sheath 11 enveloping one or more lumens 17. The invasive medical device 10 may comprise any suitable number of such lumens 17 (four lumens 17 are shown in FIG. 2 by way of non-limiting example), e.g. may in at least some embodiments include additional lumens through which instruments or the like in the device tip 15 at a distal end of the invasive medical device 10 may be controlled, e.g. through control wires running through these lumens.

The flexible sheath 11 may comprise one or more polymer layers, with at least the outer surface, i.e. the patient-facing surface, of the flexible sheath 11 comprising a biocompatible polymer such as PTFE, polyamide, polyurethane or Pebax. Other suitable biocompatible polymers will be immediately apparent to the skilled person and it should be understood that the polymers used in the flexible sheath 11 are not particularly limited. The flexible sheath 11 may further comprise a metal braiding 12 to reinforce the flexible sheath 11, e.g. to give the flexible sheath 11 the desired stiffness in order to manoeuver the invasive medical device 10 through the body of a patient, e.g. through the cardiovascular system of the patient, in a controlled manner. Such a metal braiding 12 may be made of any suitable metal or metal alloy, such as for example stainless steel, aluminium, titanium, and so on.

The flexible sheath 11 further comprises a deformable section 13 housing a deformable actuator 21, which actuator 21 typically forms part of an electrically conductive wire that loops through one or more of the lumens 17 of the invasive medical device 10 and that may be connected to an electrical current supply, e.g. in the handle (not shown) fitted at the proximal end of the invasive medical device 10 or in a separate control unit connected to the invasive medical device 10 through a cable or the like. The electrical current supply may be a mains-powered or battery-powered electrical current supply and is typically controlled by a user interface, e.g. a joystick or the like, through which an operator of the invasive medical device 10 can control the steering of the device tip 15 of the invasive medical device 10 by controllably deforming the deformable actuator 21 in the deformable section 13 with the electrical current supply, as is well-known per se.

The deformable actuator 21 in a first set of embodiments comprises a shape memory material such as a shape memory alloy (SMA), i.e. an alloy which shape can be altered using an electromechanical stimulus, e.g. through resistive heating by applying an electrical current through the deformable actuator 21. Any suitable shape memory alloy, such as a copper-aluminium-nickel or a nickel-titanium alloy may be used. Other alloys, such as zinc-copper-gold-iron alloys, iron-manganese-silicon alloys, cupper-zinc-aluminium alloys, cupper-aluminium-nickel alloys, and so on. Nickel-titanium alloys are particularly preferred due to their stability and practicality although it should be understood that any suitable shape memory alloy may be used for the deformable actuator 21. As previously explained, SMAs and in particular nickel-titanium alloys change from austenite to martensite upon cooling. As the phase changes of such SMAs and their control are well-known per se, this is not explained in further detail for the sake of brevity only.

The deformable actuator 21 in a second set of embodiments comprises an EAP. Electroactive polymers (EAPs) are an emerging class of materials within the field of electrically responsive materials. EAPs can work as sensors or actuators and can easily be manufactured into various shapes allowing easy integration into a large variety of systems. Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation. The improved performance and particular advantages of EAP materials give rise to applicability to new applications.

An EAP-based actuator 21 can be used in any application in which a small amount of movement of a component or feature is desired, based on electric actuation. The use of EAPs enables functions that were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz. Devices using electroactive polymers can be subdivided into field-driven and ionic-driven materials.

Examples of field-driven EAPs include Piezoelectric polymers, Electrostrictive polymers (such as PVDF-based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

In embodiments of the invention, the deformable actuator 21 comprises at least one field-driven electroactive material actuator. Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes). Both classes of EAP have multiple family members, each having their own advantages and disadvantages.

A first notable subclass of field-driven EAPs includes Piezoelectric and Electrostrictive polymers. While the electromechanical performance of traditional piezoelectric polymers is limited, a breakthrough in improving this performance has led to PVDF relaxor polymers, which show spontaneous electric polarization (field-driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field-driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

In some cases, thin film electrodes may be added when the polymer itself lacks sufficient conductivity (dimension-wise). The electrolyte can be a liquid, a gel or a solid material (i.e. complex of high molecular weight polymers and metal salts). Most common conjugated polymers are polypyrrole (PPy), Polyaniline (PANi) and polythiophene (PTh).

In an embodiment, the invasive medical device 10 comprises a plurality of individually addressable deformable actuators 21, which may be individually selected from SMA actuators and EAP actuators. Preferably, the deformable actuators 21 are all of the same type, e.g. all SMA actuators or all EAP actuators in order to facilitate straightforward electrical actuation of such deformable actuators 21, i.e. each deformable actuator 21 may be actuated by the same electrical stimulus. In this embodiment, the deformable actuators 21 may be located in the same deformable region 13 of the flexible sheath 11 or may be distributed across multiple deformable regions 13 of the flexible sheath 11 in order to increase the number of steerable areas of the invasive medical device 10. Where multiple individually addressable actuators 21 are present in the same deformable region 13 of the flexible sheath 11, the actuators 21 may act as antagonists for each other as previously explained.

According to the present invention, each deformable actuator 21 is anchored to the flexible sheath 11 by an adhesive-filled aperture extending through the flexible sheath 11 and exposing part of the lumen 17 housing the deformable actuator 21 or part thereof. This will be explained in further detail with the aid of FIG. 3, which depicts a manufacturing method of such an invasive medical device 10. The method begins in step a) with the provision of a completed shaft of the invasive medical device 10, which as explained before may be manufactured in any suitable manner, e.g. assembling several polymer extrusions on mandrels, after which the extrusions are braided and laminated at elevated temperatures in order to form the flexible sheath 11 enveloping one or more lumens 17, or any other conventional manufacturing method of such an invasive medical device shaft.

Figure 3:
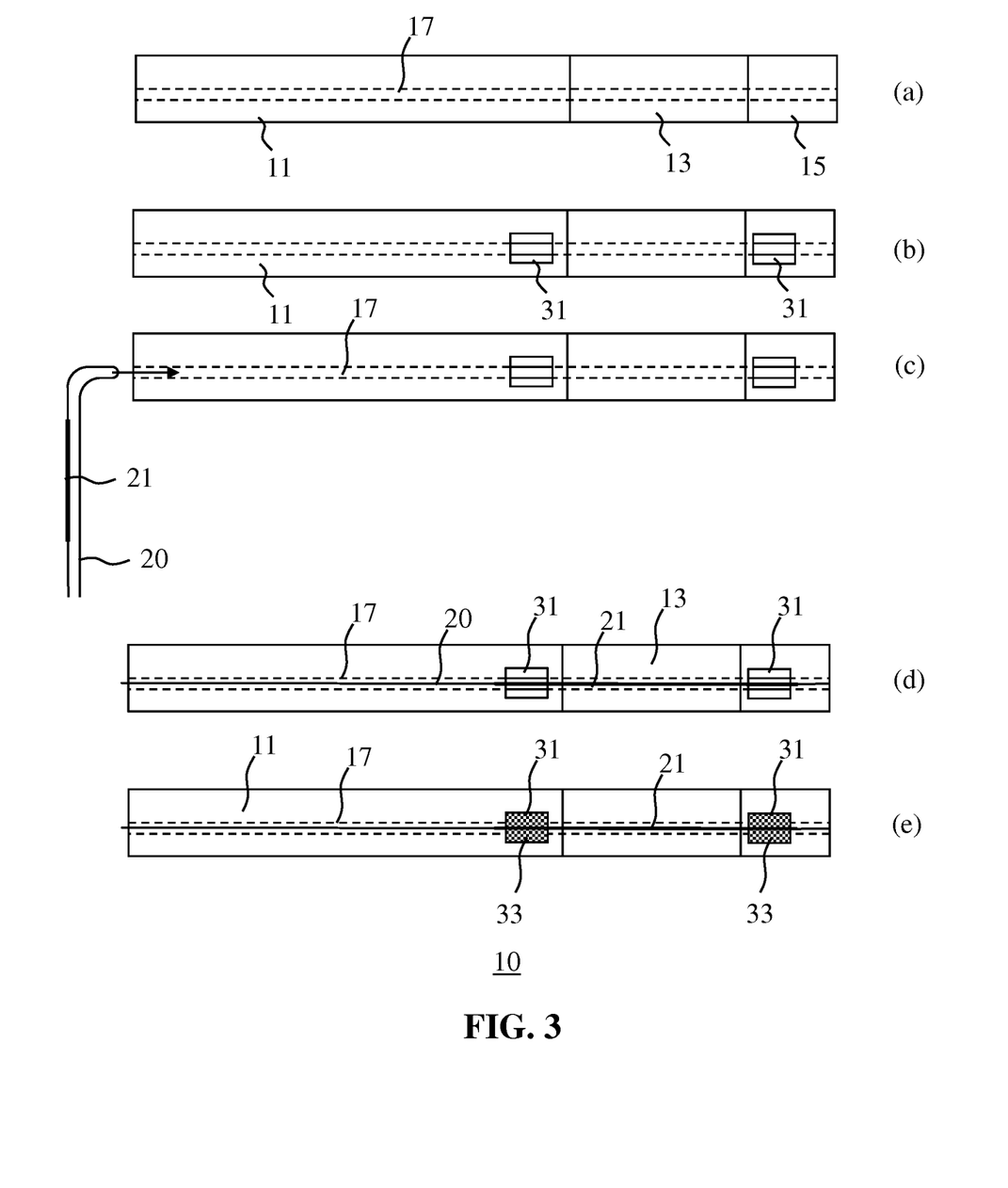
FIG. 3 schematically depicts an embodiment of a method of manufacturing an elongate flexible invasive medical device.
Figure 4:
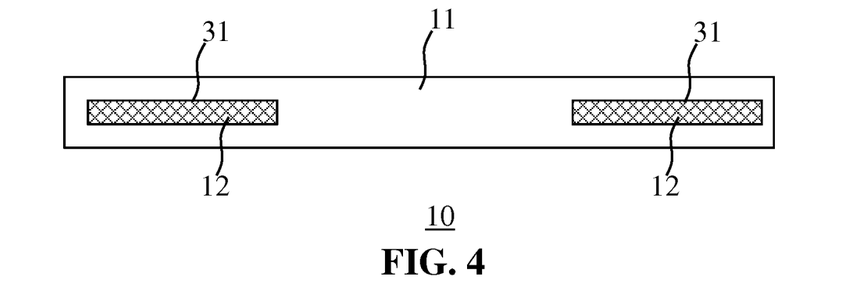
FIG. 4 schematically depicts an aspect of such a manufacturing method.

Next, in step b) a plurality of apertures 31 are cut into the flexible sheath 11 to expose regions of an underlying lumen 17 in which a deformable actuator 21 is to be anchored to the flexible sheath 11. Such apertures 31 or through holes may be cut, e.g. drilled, in any suitable manner and may have any suitable shape. For example, the apertures 31 may be shaped as elongated slits extending in the elongation direction of the invasive medical device 10. In a particularly advantageous embodiment, the apertures 31 are cut using laser cutting, for example using a pulsed laser, e.g. using Femto laser ablation. This has the advantage that the amount of energy directed at the region of the flexible sheath 11 in which the aperture 31 is to be formed can be accurately controlled, such that for example the polymer(s) of the flexible sheath 11 in this region can be selectively removed, e.g. through evaporation, whilst the metal braiding 12 in this region is kept intact, as is schematically depicted in FIG. 4, which shows apertures 31 in a section of the flexible sheath 11 in which the metal braiding 12 is intact within the apertures 31. Consequently, the structural integrity, e.g. flexural rigidity, of the invasive medical device 10 in the sections of the flexible sheath 11 in which the apertures 31 are formed is largely unaffected by the formation of these apertures 31 due to the retention of the metal braiding 12 in these apertures.

After formation of the apertures 31, the method proceeds to step c) in which the deformable actuator 21 is inserted, e.g. pulled, into the lumen 17 that is partially exposed by the apertures 31. To this end, a conductive wire 20 comprising the deformable actuator 21 is inserted into the lumen 17 at the proximal end of the invasive medical device 10, i.e. the end opposite the distal tip 15. In embodiments in which the deformable actuator 21 is a SMA-based actuator, the deformable actuator 21 may be inserted in its stretched phase (i.e. the detwinned or deformed martensite phase), such that no need exists to stretch the invasive medical device 10 afterwards. The deformable actuator 21 typically is connected to a pair of interconnect wires at opposite ends of the deformable actuator 21, which together form the conductive wire 20. The interconnect wires may define a loop within the lumen 17 such that both wires terminate at the proximal end of the invasive medical device 10, such that they may be connected to terminals of an electrical current supply in order to stimulate or actuate the deformable actuator 21 during use of the invasive medical device 10 in interventional procedures. Any suitable conductive material, e.g. any suitable metal or metal alloy, may be used for the interconnect wires of the conductive wire 20.

The insertion of the conductive wire 20 is continued until the deformable actuator 21 is precisely aligned with the apertures 31 as depicted in step d). Next, the apertures 31 are filled with an adhesive 33 such that the adhesive 33 contacts both the exposed portions of the deformable actuator 21 and the flexible sheath 11 such that upon curing of the adhesive 33 the deformable actuator 21 is anchored to the flexible sheath 11 by the adhesive 33. This results in an invasive medical device having a deformable, i.e. steerable, section 13 delimited by the anchor points, i.e. the adhesive-filled apertures 31 as the electrical current-induces deformation of the deformable actuator 21 is transferred to the section 13 through these anchor points, as will be readily understood by the skilled person. In this manner, a longitudinal section 13, i.e. a section extending in the elongation direction of the invasive medical device 10, of the flexible sheath 11 may be bent, causing bending or steering of the distal tip 15 of the invasive medical device 10.

The adhesive 33 typically can be cured below a critical temperature at which the physical state of the deformable actuator 21 is altered, e.g. where a SMA-based actuator changes shape or where an EAP-based actuator starts to degrade. For example, the adhesive 33 may be curable at room temperature. Any suitable adhesive 33 may be used for this purpose. The adhesive 33 may be a biocompatible adhesive, such for example a biocompatible epoxy adhesive, medical grade Loctite as marketed by the Henkel Corporation, biocompatible silicone adhesives, biocompatible polyurethane or acrylate adhesives, and so on. Many more biocompatible adhesives 33 will be immediately apparent to the skilled person. The use of a biocompatible adhesive 33 has the advantage that no additional measures need to be taken to protect the body of the patient from coming into contact with the adhesive 33 as the adhesive 33 is biocompatible.

Figure 5:
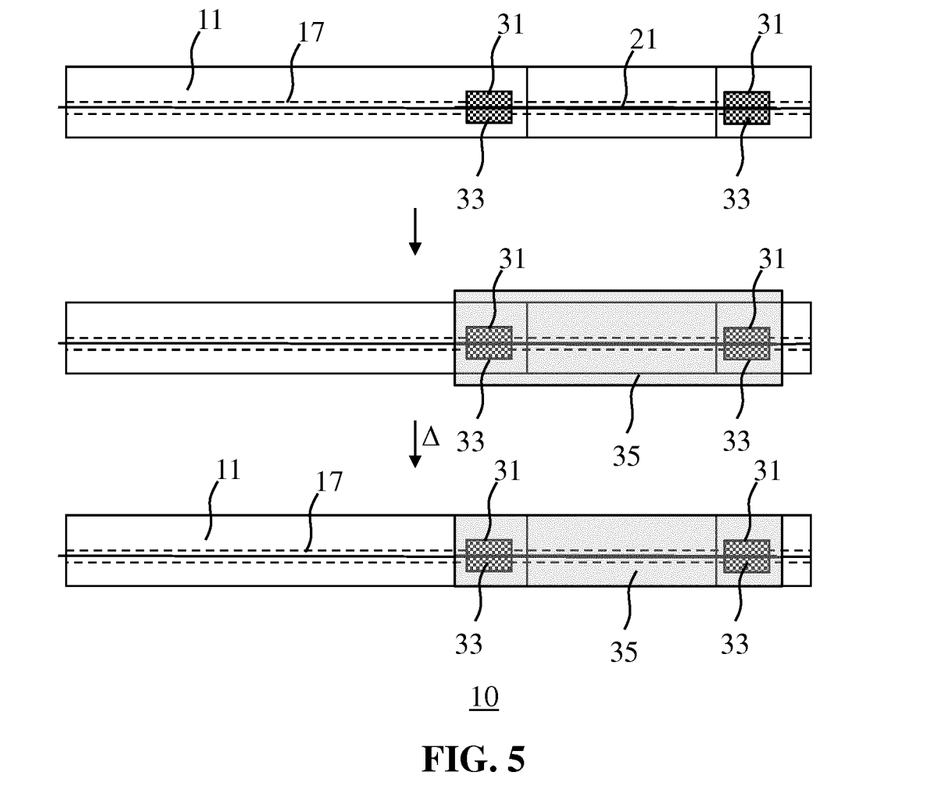
FIG. 5 schematically depicts another embodiment of a method of manufacturing an elongate flexible invasive medical device.

However, where the adhesive 33 is not biocompatible, the regions of the flexible sheath 33 containing the adhesive-filled apertures 31 may be covered by a biocompatible coating, as schematically depicted in FIG. 5. For example, a heat shrink polymer wrap 35 may be slid over the section of the flexible sheath 11 comprising the apertures 31 including the adhesive 33 and shrunk tightly around this section of the flexible sheath 11 by heating in order to form the biocompatible coating around this section of the flexible sheath 11. It should be understood that alternatively such a heat shrink polymer wrap 35 may envelop the entire flexible sheath 11 although this is not preferred as the flexibility of the flexible sheath 11 may be altered by the presence of such a heat shrink polymer wrap 35. Any suitable biocompatible polymer or polymer blend may be used for such a heat shrink wrap 35. Non-limiting examples of such biocompatible polymers include PE, PP, PET, PTFE and so on. Many other suitable examples of such biocompatible polymers will be immediately apparent to the skilled person.

At this point, it is noted that although the above manufacturing method describes the insertion of a single conductive wire 20 into a single lumen 17, it should be understood that this procedure may be repeated to insert multiple deformable actuators 21 into multiple lumens 17 as previously explained. For example the section 13 may comprise a pair of SMA-based actuators 21 that act as antagonists for each other, such that a shrunk actuator 21, i.e. an actuator 21 phase-transferred to its twinned martensite phase via the austenite phase, can be stretched to its detwinned martensite phase by actuating the opposing SMA-based actuator 21, thereby bending the device tip 15 in the opposite direction.

Figure 6:
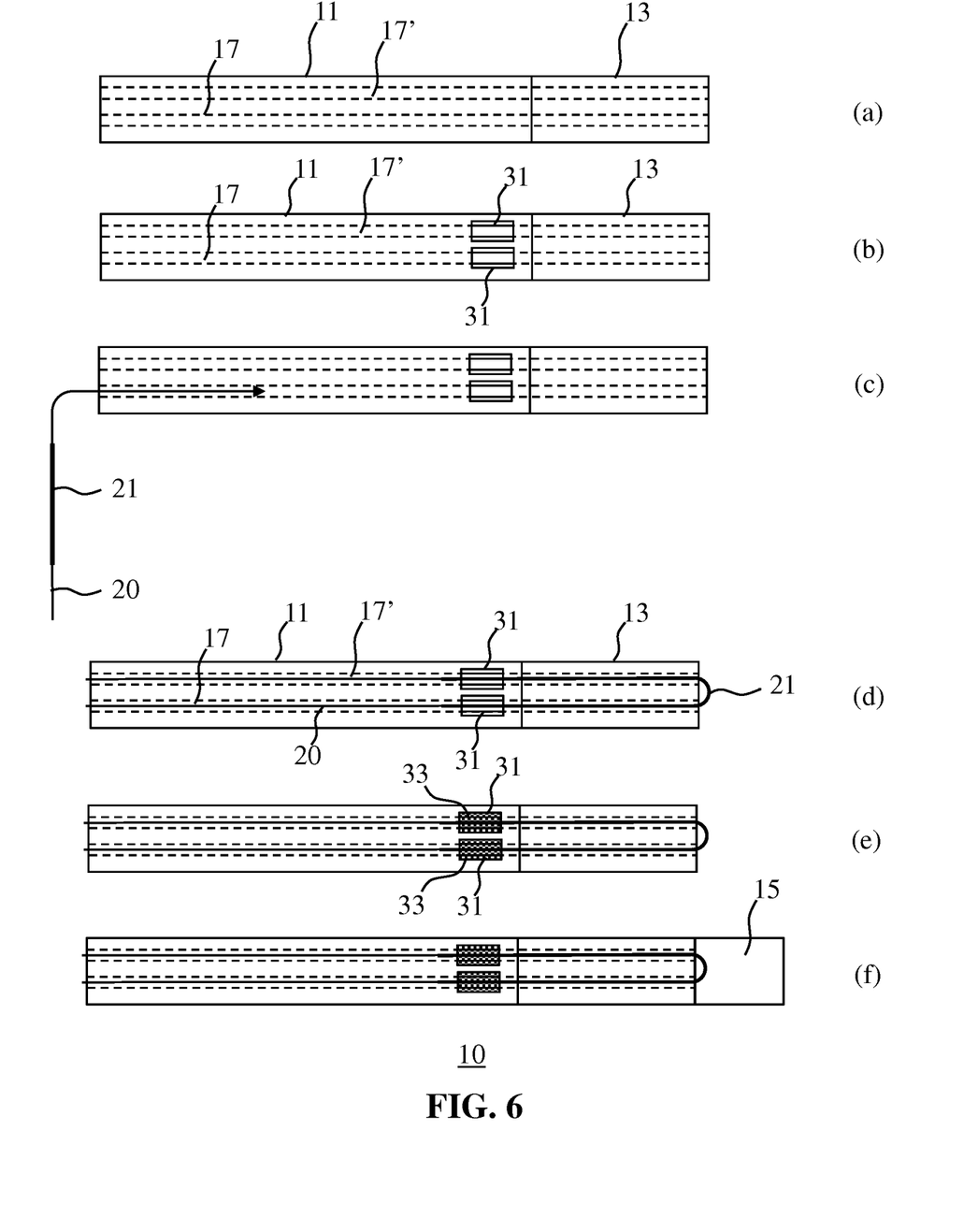
FIG. 6 schematically depicts yet another embodiment of a method of manufacturing an elongate flexible invasive medical device.

In yet another embodiment, the deformable actuator 21 may be looped across a pair of lumens 17, 17', as depicted in FIG. 6, which schematically depicts a manufacturing method for such an invasive medical device 10. The reference numerals in FIG. 6 have the same meaning as previously described for FIG. 3 and are therefore not described again for the sake of brevity. In this embodiment, the finished shaft of the invasive medical device 10 is provided without the distal tip 15 in step a), after which the apertures 31 are formed in the flexible sheath 11 in step b) as previously explained. However, in this embodiment, the apertures or through-holes 31 are located proximal to the proximal end of the flexible sheath 11, and expose different lumens 17 and 17' within the flexible sheath 11.

Next, the conductive wire 20 including the deformable actuator 21 is inserted into the first lumen 17 at the proximal end of the invasive medical device 10 in step c) and the deformable actuator is looped back into the second lumen 17' in step d) such that a first portion of the deformable actuator 21 is located within the first lumen 17 and a second portion of the deformable actuator 21 is located within the second lumen 17', with a first interconnect wire extending from the first portion of the deformable actuator 21 to the proximal end of the invasive medical device 10 through the first lumen 17 and a second interconnect wire extending from the second portion of the deformable actuator 21 to the proximal end of the invasive medical device 10 through the second lumen 17'. Alternatively, the conductive wire 20 including the deformable actuator 21 may be inserted into the first lumen 17 and the further lumen 17' from the distal end of the invasive medical device 10 as will be readily understood by the skilled person.

In step e), the adhesive 33 is applied to the apertures 31 such that the first and second portions of the deformable actuator 21 are anchored to the flexible sheath 11 after curing the adhesive 33, after which the invasive medical device 10 is finished by securing the distal tip 15 to the flexible sheath 11 at its distal end, e.g. using a suitable adhesive or the like. In this embodiment of the invasive medical device 10, the presence of two deformable actuator portions in adjacent lumens 17, 17' ensures a larger deformation force can be applied to the deformable portion of the flexible sheath 11, whilst requiring only two fixation points, i.e. adhesive regions 33, are required to secure the paired actuator portions in the flexible sheath.

With the assembly method according to the above described embodiments, it has been proven possible to construct steerable invasive medical devices having a diameter of less than 1 mm that include SMA-based actuators 21, and that exhibit superior performance compared to such invasive medical devices, e.g. catheters, manufactured using conventional assembly techniques.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An invasive medical device comprising a flexible sheath enveloping at least one lumen, said at least one lumen comprising an electrically conductive wire including a deformable actuator for deforming a section of the invasive medical device in response to an electric current provided through the electrically conductive wire, wherein the flexible sheath comprises a set of apertures extending through the flexible sheath to the at least one lumen, said apertures being filled with an adhesive anchoring the deformable actuator to the flexible sheath.

2. The invasive medical device of claim 1, wherein the deformable actuator comprises a shape memory material.

3. The invasive medical device of claim 1, wherein the deformable actuator comprises an electro-actuated polymer.

4. The invasive medical device of claim 1, further comprising a biocompatible sleeve around a section of the flexible sheath comprising the set of apertures.

5. The invasive medical device of claim 4, wherein the biocompatible sleeve comprises a shrink wrap polymer.

6. The invasive medical device of claim 1, wherein the at least one lumen comprises:
   a first lumen comprising a first electrically conductive wire including a first deformable actuator; and
   a further lumen comprising a further electrically conductive wire including a further deformable actuator.

7. The invasive medical device of claim 1, wherein the at least one lumen comprises:
   a first lumen comprising a portion of the electrically conductive wire including a portion of the deformable actuator; and
   a further lumen comprising a further portion of the electrically conductive wire including a further portion of the deformable actuator.

8. The invasive medical device of claim 7, wherein the flexible sheath comprises a polymer reinforced by a metal braiding, said adhesive extending through the metal braiding.

9. The invasive medical device of claim 8, wherein the invasive medical device is a multi-lumen catheter or a guide wire.

\* \* \* \* \*